(12) United States Patent
Karimi et al.

(10) Patent No.: US 8,309,770 B2
(45) Date of Patent: Nov. 13, 2012

(54) 11C-LABELED BENZOPHENONE/BENZOXAZOLE ANALOGUES AS AN INFLAMMATION IMAGING AGENT

(75) Inventors: Farhad Karimi, Mansfield, MA (US); Bengt Langstrom, Uppsala (SE)

(73) Assignee: GE Healthcare Limited, Buckinghamshire (GB)

( * ) Notice: Subject to any disclaimer, the term of this patent is extended or adjusted under 35 U.S.C. 154(b) by 593 days.

(21) Appl. No.: 12/301,497

(22) PCT Filed: May 21, 2007

(86) PCT No.: PCT/IB2007/001311
§ 371 (c)(1),
(2), (4) Date: Nov. 23, 2009

(87) PCT Pub. No.: WO2007/135541
PCT Pub. Date: Nov. 29, 2007

(65) Prior Publication Data
US 2010/0063298 A1    Mar. 11, 2010

Related U.S. Application Data

(60) Provisional application No. 60/802,416, filed on May 22, 2006.

(51) Int. Cl.
*C07C 49/786*    (2006.01)

(52) U.S. Cl. .......................................... 568/333

(58) Field of Classification Search ................. 548/221; 568/333
See application file for complete search history.

(56) References Cited

FOREIGN PATENT DOCUMENTS
WO        2005/120584        12/2005

OTHER PUBLICATIONS

Lidstrom, Pelle, et.al. "[11C]Carbon monoxide in the palladium-mediated synthesis of 11C-labelled ketones" Journal of the Chemical society, Perkin Transactions 1., 1997, pp. 2701-2706.
Nader, M.W., et.al. "Synthesis of [carbonyl-<11>c]2-(2-benzoylphenoxy)-N-phenylacetamide from [<11>C]carbon monoxide by the suziki and the stille reactions" Applied Radiation and Isotopes, Elsevier, Oxvord, GB, vol. 57, No. 5, Nov. 2002 pp. 681-685.
Khanum, et.al. "Synthesis and anti-inflammatory activity of benxophenone analogues" Bioorganic Chemistry, vol. 32, No. 4, Aug. 2004, pp. 211-222.
Unlu, et.al. "Studies on novel 7-acyl-5-chloro-2-oxo-3H-benzoxazole derivatives as potential analgesic and anti-inflammatory agents" Archiv der pharmazie, VCH Verlagsgelsellschaft MBH, Weinheim, DE, vol. 336, No. 6/7, 2003, pp. 310-321.
PCT/IB2007/001311 Int'l Search Report/Written Opinion dated Oct. 2007.

*Primary Examiner* — Kristin Bianchi
(74) *Attorney, Agent, or Firm* — Yonggang Ji

(57) ABSTRACT

A method of preparing novel [$^{11}$C]-labeled benzophenone/bezoxazole analogues is provided. The present invention also provides novel [$^{11}$C]-labeled benzophenone/bezoxazole analogues prepared from the GMP synthesis method. Kit claims for preparing novel [$^{11}$C]-labeled benzophenone/bezoxazole analogues and a method of use thereof are also provided.

4 Claims, No Drawings

11C-LABELED BENZOPHENONE/BENZOXAZOLE ANALOGUES AS AN INFLAMMATION IMAGING AGENT

This application is a filing under 35 U.S.C. 371 of international application number PCT/IB2007/001311, filed May 21, 2007, which claims priority to application number 60/802,416 filed May 22, 2006, in The United States the entire disclosure of which is hereby incorporated by reference.

FIELD OF THE INVENTION

The present invention relates to a synthesis method of preparing [$^{11}$C]-labeled benzophenone/bezoxazole analogues. The present invention also relates to [$^{11}$C]-labeled benzophenone/bezoxazole analogues prepared from the synthesis method. The present invention further relates to kits for preparing [$^{11}$C]-labeled benzophenone/bezoxazole analogues as well as the use of preparing the same. A preclinical evaluation of the labeled analogues will be performed to verify the expected biological properties.

BACKGROUND OF THE INVENTION

A group of diagnostic Positron Emission Tomography ("PET") procedures utilize radioactive labeled compounds, wherein the radioactive atoms are positron emitters. Some examples of positron emitting elements include nuclides of carbon, nitrogen, or fluorine. These elements are the backbone of almost all biological active compounds. In order to be able to use these elements, stable isotopes are replaced with a radioactive isotope. The radioactive labeled compounds, called tracers, are transported, accumulated and converted exactly the same way as for non-radioactive compounds. The PET method has possibilities to detect malfunction on a cellular level in the investigated tissues or organs. The method is very sensitive and requires only nanomole quantities of produced radioactive tracers. These radioactive tracers have a half-life in the range from 2 to 110 minutes, (e.g. $^{11}$C, $t_{1/2}$=20.4 min). Karimi et al., *Eur. J. Org. Chem.*, 2005, 2374-2378, *Acta Upsaliensis, Uppsala* 2002, ISBN 91-554-5452-6 and Rahman et al., *Eur. J. Org. Chem.*, 2004, 2674-2678. Because of the radioactivity, the short half-lives and the submicromolar amounts of the labeled substances, extraordinary synthetic procedures are required for the production of these tracers. The most used precursors for the introduction of $^{11}$C in a bioactive molecule are [$^{11}$C] iodomethane and [$^{11}$C] methyl triflate used in methylation reactions, [$^{11}$C] carbon dioxide in the Grignard reaction, and [$^{11}$C] carbon monoxide in carbonylation reactions. Additionally, an important part of the elaboration of these procedures is the development and handling of new anti-inflammatory [$^{11}$C]-labeled tracers.

Inflammatory responses are thought to be mediated in part by the prostaglandins ("PGs") derived from arachidonic acid by the action of prostaglandin H synthase, which is also referred to as cyclooxygenase ("COX"). Khanum et al., *Bioorg. Chem.*, 2004, vol. 32, 211-222.

Recent studies have shown that COX exists in two isoforms COX-1 and COX-2. Both COX are constitutively expressed in most tissues, but COX-2, in contrast COX-1, is the mitogen inducible isoform. The inducing stimuli for COX-2 include pro-inflammatory cytokines and growth factors, implying a role for COX-2 in both inflammation and control of cell growth. COX isoforms are almost identical in structure but have important differences in substrate and inhibitor selectivity and in their intercellular locations. Protective PGs which preserve the integrity of the stomach lining and maintain normal renal function in a compromised kidney, are synthesized by COX-1. In addition to the induction of COX-2 in inflammatory lesions, it is present constitutively in the brain and spinal cord, where it may be involved in the nerve transmission, particularly those for pain and fever. Khanum et al., *Bioorg. Chem.*, 2004, vol. 32, 211-222.

COX is the principal target of nonsteroidal anti-inflammatory drugs ("NSAIDs") and metabolites of the COX pathway are widely accepted as mediators of the inflammatory response. NSAIDs block the formation of PGs and have anti-inflammatory, analgesic, and antipyretic activity. The discovery of COX-2 has made it possible to design drugs that reduce inflammation without removing the protective PGs in the stomach and kidney made by COX-1. Khanum et al., *Bioorg. Chem.*, 2004, vol. 32, 211-222.

Benzophenone analogues have been identified as potent anti-inflammatory agents. Welstead et al. and Branacaccio et al. have reported the anti-inflammatory activity of benzoylphenylacetic acid. Khanum et al., *Bioorg. Chem.*, 2004, vol. 32, 211-222.

In addition, Vigorita et al. have identified polyaromatic trifluoroacetamides as anti-inflammatory agents. Vigorita et al., *Farmaco*, 1989, vol. 46, 1074-1079. Accordingly, Khanum et al. synthesized hydroxybenzophenones, aroyl aryloxyacetic acid and acetamide analogues, and evaluated them for their anti-inflammatory activity and side effects. Khanum et al., *Bioorg. Chem.*, 2004, vol. 32, 211-222. Additionally, Unlu et al. synthesized a series of alkanoic acid derivatives and evaluated their analgesic and anti-inflammatory activities. Khanum et al., *Bioorg. Chem.*, 2004, vol. 32, 211-222.

Based on the aforementioned, there is a need to find better radioactive yields, trapping efficiency, and shorter reaction times for [$^{11}$C]-labeled benzophenone/benzoxazole analogues.

Furthermore, there is a need for creating inflammation imaging agents wherein these agents can be, visualized by PET.

Discussion or citation of a reference herein shall not be construed as an admission that such reference is prior art to the present invention.

SUMMARY OF THE INVENTION

In view of the needs of the prior art, the present invention provides a method of obtaining a novel series of [$^{11}$C]-labeled benzophenone/benzoxazole analogues showing anti-inflammatory activities with the aid of positron emission tomography ("PET"). The present invention further provides these novel [$^{11}$C]-labeled benzophenone/benzoxazole analogues. The present invention also provides kits for making novel [$^{11}$C]-labeled benzophenone/benzoxazole analogues and visualizing these analogues by PET.

The [$^{11}$C]-labeled benzophenone/benzoxazole analogues of the present invention are obtained through Good Manufacturing Practice ("GMP") syntheses. GMP is part of Quality Assurance which ensures that products are consistently produced and controlled to the quality standards appropriate to their intended use and as required by the Marketing Authorization.

One embodiment of the present invention encompasses a compound of formula (I),

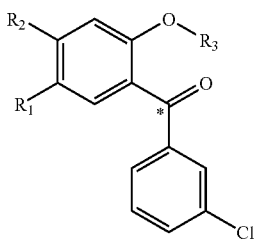

wherein, $R_1$ & $R_2$=alkyl, aryl, alkoxide, or a halide; $R_3$=H, $CH_2COOH$, $CH_2CONHR'$, or $CH_2CONR'R''$ wherein R' or R" is alkyl, aryl, or a combination thereof.

Another embodiment of the present invention is a compound of formula (II),

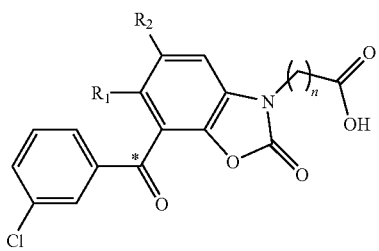

wherein $R_1$ & $R_2$=Alkyl, aryl, alkoxide, halide, or a combination thereof, and wherein n=1, 2, or 3.

Yet an additional embodiment of the present invention is a method for preparing compound (I), comprising the steps:

flushing a solution of tris(dibenzylideneactone)palladium (0) and tri-o-tolylphosphine in anhydrous DMSO with nitrogen to form a mixture; then adding either a halide, halide salt, or triflate to the mixture; thereafter filtering (ThermoHypersil F2513-3, syringe filter 0.45 μm) the mixture; next adding either boronic acid or an organostannyl compound to form a compound mixture; then injecting the compound mixture into a microautoclave to form a crude product; finally transferring the crude product to a vial at reduced pressure whereby the crude product is then diluted with water and thereafter the crude product is purified and identified by positron emission tomography.

A further embodiment of the invention is a method for preparing compound (II), comprising the steps:

flushing a solution of tris(dibenzylideneactone)palladium (0) and tri-o-tolylphosphine in anhydrous DMSO with nitrogen to form a mixture; then adding a halide, halide salt, or triflate to the mixture; thereafter filtering the mixture; next adding either boronic acid or an organostannyl compound to form a compound mixture; then injecting the compound mixture into a microautoclave to form a crude product; finally transferring the crude product to a vial at reduced pressure whereby the crude product is then diluted with water and thereafter the crude product is purified and identified by positron emission tomography.

Another embodiment of the present invention encompasses a kit for preparing a compound of formula (I), wherein the kit comprises the steps of:

flushing a solution of tris(dibenzylideneactone)palladium (0) and tri-o-tolylphosphine in anhydrous DMSO with nitrogen to form a mixture; then adding either a halide, halide salt, or triflate to the mixture; thereafter filtering the mixture; next adding either boronic acid or an organostannyl compound to form a compound mixture; then injecting the compound mixture into a microautoclave to form a crude product; finally transferring the crude product to a vial at reduced pressure whereby the crude product is then diluted with water and thereafter the crude product is purified and identified by positron emission tomography.

Yet a further embodiment of the present invention is a kit for preparing a compound of formula (II), wherein the kit comprises the steps of:

flushing a solution of tris(dibenzylideneactone)palladium (0) and tri-o-tolylphosphine in anhydrous DMSO with nitrogen to form a mixture; then adding either a halide, halide salt, or triflate to the mixture; thereafter filtering the mixture; next adding either boronic acid or an organostannyl compound to form a compound mixture; then injecting the compound mixture into a microautoclave to form a crude product; finally transferring the crude product to a vial at reduced pressure whereby the crude product is then diluted with water and thereafter the crude product is purified and identified by positron emission tomography.

DETAILED DESCRIPTION OF THE INVENTION

Due to the short half-life, low reactivity, and solubility of [$^{11}$C] carbon monoxide, one-pot carbonylation reactions using a micro-autoclave is preferred, and various types of $^{11}$C-carbonyl compounds have been synthesized by this approach. In the present invention, anti-inflammatory activity of [$^{11}$C]-labeled benzophenone/benzoxazole analogues was studied. These analogues showed significant anti-inflammatory profile with low gastric ulceration incidence. The present invention sets forth several additional advantages over prior methods.

The current method presents an ease of use over other methods, half the total synthesis and cycle time used in previous methods as well as obtaining a higher radiochemical yield when excess [$^{11}$C]-labeled benzophenone/benzoxazole analogues were obtained. This excess in effect generated an increased trapping efficiency compared to previous methods as well. Accordingly, the radiochemical yields of the [$^{11}$C]-labeled benzophenone/benzoxazole compounds when using an organostannyl compound were in the range of about 50% to about 99%. The corresponding trapping efficiencies, however, were on average 22% lower than the radiochemical yields. Furthermore, the radiochemical yields when using a boronic acid produced about 10% lower radiochemical yield of the [$^{11}$C]-labeled benzophenone/benzoxazole compounds and about 15% lower trapping efficiency. The trapping efficiency disclosed herein indicates the amount of incorporated $^{11}$C in the crude product, i.e. the fraction of radioactivity left in the crude product after purging with nitrogen gas.

Additionally, a shorter synthesis time is important for efficiently supplying a

PET center with radioactive precursor batches needed for synthesis of tracers for PET-scans. Short synthesis times will also yield compounds with higher radiochemical yield and specific radioactivity (Becquerel/mole) due to less decay. Radiochemical yield (purity) is defined as the amount of radioactivity originating from a specific substance in relation to the total amount of radioactivity in a sample, expressed in %. Additionally, specific radioactivity (Becquerel/mole) is the ratio between the amount of radioactivity originating from a specific substance labeled with a radionuclide and the total amount of that specific substance.

Furthermore, there is a need for a rapid efficient alternative method for $^{11}$C-labeling of ketones owing to the variation in reported radiochemical yields. In the present inventions method to prepare [$^{11}$C]-labeled benzophenone/benzoxazole analogues, a palladium complex was used and all reactions were preformed at 125 degrees C. A reaction time of about 2 minutes to about 5 minutes was used. The results indicated that the choice of analogue and solvent have a major impact on the radiochemical yield. For instance, using DMSO as a solvent instead of DMF increased the radiochemical yield from about 8% to about 50%.

In one embodiment of the present invention a compound of formula (I),

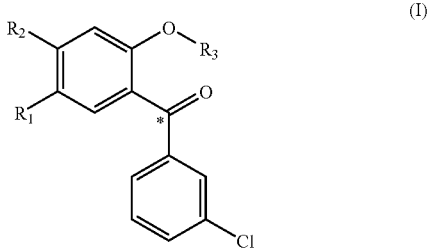

(I)

wherein, $R_1$ & $R_2$=alkyl, aryl, alkoxide, or a halide; $R_3$=H, $CH_2COOH$, $CH_2CONHR'$, or $CH_2CONR'R''$ wherein R' or R" is alkyl, aryl, or a combination thereof is disclosed.

In another embodiment of the present invention, a compound of formula (II),

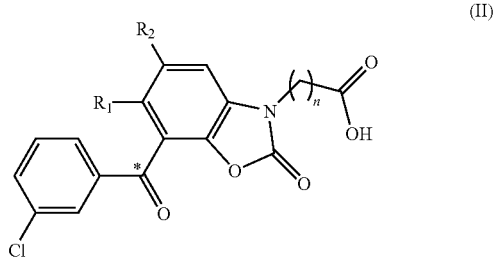

(II)

wherein $R_1$ & $R_2$=Alkyl, aryl, alkoxide, halide, or a combination thereof, and wherein n=1, 2, or 3 is disclosed.

Yet in a further embodiment a method for preparing compound (I), comprising the steps:

flushing a solution of tris(dibenzylideneactone)palladium (0) and tri-o-tolylphosphine in anhydrous DMSO with nitrogen to form a mixture; then adding either a halide, halide salt, or triflate to the mixture; thereafter filtering the mixture; next adding either boronic acid or an organostannyl compound to form a compound mixture; then injecting the compound mixture into a microautoclave to form a crude product; finally transferring the crude product to a vial at reduced pressure whereby the crude product is then diluted with water and thereafter the crude product is purified and identified by positron emission tomography is disclosed.

An additional embodiment of the present invention depicts a method for preparing compound (II), comprising the steps:

flushing a solution of tris(dibenzylideneactone)palladium (0) and tri-o-tolylphosphine in anhydrous DMSO with nitrogen to form a mixture; then adding a halide, halide salt, or triflate to the mixture; thereafter filtering the mixture; next adding either boronic acid or an organostannyl compound to form a compound mixture; then injecting the compound mixture into a microautoclave to form a crude product; finally transferring the crude product to a vial at reduced pressure whereby the crude product is then diluted with water and thereafter the crude product is purified and identified by positron emission tomography.

A further embodiment depicts a method of compound (I) wherein the tris(dibenzylideneactone)palladium (0) is a catalyst.

Another embodiment of the present invention depicts a method of compound (I) wherein the halide is aryl.

Yet a further embodiment depicts a method of compound (I) wherein the triflate is aryl.

Additionally, an embodiment of the present invention shows a method of compound (I), wherein the boronic acid is aromatic or aliphatic. Yet a further embodiment shows a method of compound (I), wherein the organostannyl compound is aliphatic.

A further embodiment discloses a method of compound (I), wherein the microautoclave is pressurized from about 30 to about 40 MPa and a reduced pressure within the vial is about 10 MPa to about 50 MPa.

Another embodiment of the present invention depicts a method of compound (II), wherein the wherein the tris(dibenzylideneactone)palladium (0) is a catalyst.

A further embodiment of the invention depicts a method according to compound (II), wherein the halide is aryl.

An additional embodiment shows a method according to compound (II), wherein the triflate is aryl wherein the boronic acid is aromatic or aliphatic and wherein the organostannyl compound is aliphatic.

A further embodiment shows a method according to compound (II), wherein the microautoclave is pressurized from about 30 to about 40 MPa.

Another embodiment of the present invention depicts a method according to compound (II), wherein the reduced pressure within the vial is about 10 MPa to about 50 MPa.

Yet a further embodiment of the present invention shows a kit for preparing a compound of formula (I), wherein the kit comprises the steps of:

flushing a solution of tris(dibenzylideneactone)palladium (0) and tri-o-tolylphosphine in anhydrous DMSO with nitrogen to form a mixture; then adding either a halide, halide salt, Or triflate to the mixture; thereafter filtering the mixture; next adding either boronic acid or an organostannyl compound to form a compound mixture; then injecting the compound mixture into a microautoclave to form a crude product; finally transferring the crude product to a vial at reduced pressure whereby the crude product is then diluted with water and thereafter the crude product is purified and identified by positron emission tomography.

Another embodiment of the invention shows a kit according to compound (II), wherein the tris(dibenzylideneactone) palladium (0) is a catalyst and the halide is aryl.

Yet a further embodiment of the invention depicts a kit according to compound (II), wherein the triflate is aryl and the boronic acid is aromatic or aliphatic, and the organostannyl compound is aliphatic.

Another embodiment of the invention encompasses a kit according to compound (II), wherein the microautoclave is pressurized from about 30 to about 40 MPa and the reduced pressure within the vial is about 10 MPa to about 50 MPa.

Still a further embodiment of the invention depicts a kit for preparing a compound of formula (II), wherein the kit comprises the steps of:

flushing a solution of tris(dibenzylideneactone)palladium (0) and tri-o-tolylphosphine in anhydrous DMSO with nitrogen to form a mixture; then adding either a halide, halide salt, or triflate to the mixture; thereafter filtering the mixture; next adding either boronic acid or an organostannyl compound to form a compound mixture; then injecting the compound mixture into a microautoclave to form a crude product; finally transferring the crude product to a vial at reduced pressure whereby the crude product is then diluted with water and thereafter the crude product is purified and identified by positron emission tomography.

Yet an additional embodiment of the present invention depicts a kit according to compound (II), wherein the tris (dibenzylideneactone)palladium (0) is a catalyst.

Furthermore, an additional embodiment of the invention shows a kit according to compound (II), wherein the halide is aryl, the triflate is aryl, the boronic acid is aromatic or aliphatic and the organostannyl compound is aliphatic.

Yet another embodiment of the invention shows a kit according to compound (II), wherein the microautoclave is pressurized from about 30 to about 40 MPa and the reduced pressure within the vial is about 10 MPa to about 50 MPa.

Another embodiment of the present invention depicts a method of use for preparing a compound of formula (I) or formula (II),

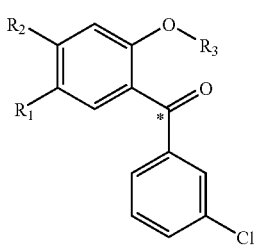

(I)

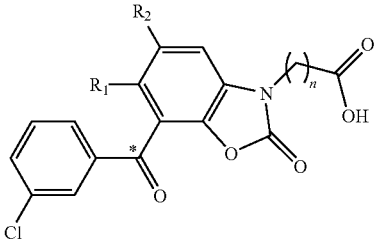

(II)

wherein formula (I), $R_1$ & $R_2$=alkyl, aryl, alkoxide, or a halide; $R_3$=H, $CH_2COOH$, $CH_2CONHR'$, or $CH_2CONR'R''$ wherein R' or R" is alkyl, aryl, or a combination thereof and wherein formula (II) wherein $R_1$ & $R_2$=Alkyl, aryl, alkoxide, halide, or a combination thereof, and wherein n=1, 2, or 3.

further wherein the method comprises the steps of:

flushing a solution of tris(dibenzylideneactone)palladium (0) and tri-o-tolylphosphine in anhydrous DMSO with nitrogen to form a mixture; then adding either a halide, halide salt, or triflate to the mixture; thereafter filtering the mixture; next adding either boronic acid or an organostannyl compound to form a compound mixture; then injecting the compound mixture into a microautoclave to form a crude product; finally transferring the crude product to a vial at reduced pressure whereby the crude product is then diluted with water and thereafter the crude product is purified and identified by positron emission tomography.

Yet another embodiment of the invention shows a method of use wherein the tris(dibenzylideneactone)palladium (0) is a catalyst.

Still a further embodiment encompasses a method of use wherein the halide is aryl and the triflate is aryl.

A further embodiment of the invention presents a method of use wherein the boronic acid is aromatic or aliphatic and wherein the organostannyl compound is aliphatic.

Another embodiment of the present invention shows a method of use wherein the microautoclave is pressurized from about 30 to about 40 MPa and the reduced pressure within the vial is about 10 MPa to about 50 MPa.

EXAMPLE 1

Experimental Studies

General Labeling Method

A capped vial (1 ml) containing a solution of tris(dibenzylideneactone)palladium (0) and tri-o-tolylphosphine in anhydrous DMSO (300 microL) was flushed with nitrogen. The reaction mixture was kept at room temperature for 10 minutes. A halide, halide salt, or a triflate, preferably an aryl triflate, was added and the resulting mixture was kept at room temperature for another 5 minutes. The reaction mixture was filtered (PTFE syringe filter 0.45 micrometers) before addition of a boronic acid or an organostannyl compound just before injection into the microautoclave pre-charged with [11C] carbon monoxide. These microautoclave reactions were achieved in a stainless steel batch reactor microautoclave system (200 microL). The micro-autoclave was heated at 100 degrees C. for 5 minutes. The crude product was transferred to a vial (3 ml) at a pressure from about 10 MPa and 50 MPa. The radioactivity was measured before and after the vial was flushed with nitrogen. The crude product was diluted with 1.5 ml of water and purified by semi-preparative liquid chromatography. The identity of the compounds and radiochemical yield (purity) were established by positron emission tomography.

The following compounds were synthesized using aryl iodide and the corresponding orgaostannyl compound. The results of the radiochemical yield and trapping efficiency of each of these compounds are as follows:

| Compound | RCY | TE |
|---|---|---|
| $^{11}$C-benzophenone | 85% | 99% |
| $^{11}$C-phenyl(pyridin-3-yl)methanone | 50% | 99% |

The two main target compounds of the present invention are depicted below. The halides and triflate compounds, the boronic acid compounds and the organostannyl compounds used in the present invention.

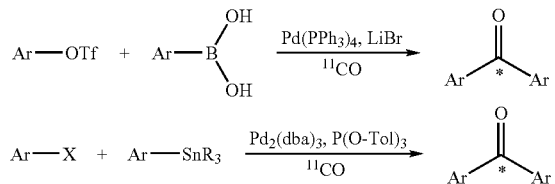

Specific Embodiments, Citation of References

The present invention is not to be limited in scope by specific embodiments described herein. Indeed, various modifications of the inventions in addition to those described herein will become apparent to those skilled in the art from the foregoing description and accompanying figures. Such modifications are intended to fall within the scope of the appended claims.

Various publications and patent applications are cited herein, the disclosures of which are incorporated by reference in their entireties.

What is claimed is:

1. A method for preparing compound (I)

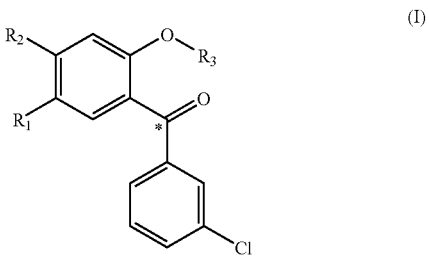

wherein, * denotes a [$^{11}$C], $R_1$ & $R_2$ = alkyl, aryl, alkoxide, or a halide; $R_3$ = H, $CH_2COOH$, $CH_2CONHR'$, or $CH_2CONR'R''$ wherein R' or R'' is alkyl, aryl, or a combination thereof, comprising the steps:

flushing a solution of tris(dibenzylideneactone) palladium (0) and tri-o- tolylphosphine in anhydrous DMSO with nitrogen to form a mixture; then adding either an aryl halide, or aryl triflate to the mixture; thereafter filtering the mixture; next adding either aromatic or aliphatic boronic acid or an aliphatic organostannyl compound to form a compound mixture; then injecting the compound mixture into a microautoclave precharged with [11C] carbon monoxide to form a crude product; finally transferring the crude product to a vial at reduced pressure whereby the crude product is then diluted with water and thereafter the crude product is purified and identified by positron emission tomography.

2. The method according to claim 1, wherein the tris(dibenzylideneactone) palladium (0) is a catalyst.

3. The method according to claim 1, wherein the microautoclave is pressurized from about 30 to about 40 MPa.

4. The method according to claim 1, wherein the reduced pressure within the vial is about 10 MPa to about 50 MPa.

* * * * *